United States Patent [19]

Higginbottom et al.

[11] Patent Number: 4,507,428
[45] Date of Patent: Mar. 26, 1985

[54] AQUEOUS DISPERSIONS OF POLYAMINES AND POLY(DIHYDROBENZOXAZINES)

[75] Inventors: Harold P. Higginbottom, Wilbraham; Manuel F. Drumm, Springfield, both of Mass.

[73] Assignee: Monsanto Company, St. Louis, Mo.

[21] Appl. No.: 581,389

[22] Filed: Feb. 17, 1984

[51] Int. Cl.³ .................. C08L 61/12; C08L 79/04
[52] U.S. Cl. ............................... 524/596; 524/595; 524/611; 528/153; 528/162; 528/172; 528/210; 528/211; 528/406; 528/407
[58] Field of Search ............... 524/611, 595, 596; 528/172, 210, 211, 153, 162, 406, 407

[56] References Cited

U.S. PATENT DOCUMENTS

| 2,825,728 | 3/1958 | Rigterink | 260/264 |
| 2,826,575 | 3/1958 | Rigterink | 260/244 |
| 3,408,326 | 10/1968 | Errede | 528/210 |
| 3,563,920 | 2/1971 | Tomalia et al. | 528/210 |
| 3,738,961 | 6/1973 | Tomalia et al. | 528/210 |

FOREIGN PATENT DOCUMENTS 1437814  6/1976  United Kingdom ............... 260/264

OTHER PUBLICATIONS

Burke et al., J. Am. Chem. Soc., 72, 4691 (1950).
Burke et al., J. Org. Chem. 26, 4403 (1961).
Burke et al., J. Org. Chem. 30, 3423 (1965).
Kuehne, J. Med. Pharm. Chem., 5, 257 (1962).
Bishop, Dissertation Summary, 63-1372, University Microfilms Inc., Ann Arbor, Michigan (1962).

Primary Examiner—Lester L. Lee
Attorney, Agent, or Firm—R. Bruce Blance; William J. Farrington; Paul D. Matukaitis

[57] ABSTRACT

An aqueous dispersion comprising a poly(3,4-dihydro-3-substituted-1,3 benzoxazine) and a protonated reactive polyamine, wherein the polyamine is at least difunctional, its reactive groups being primary or secondary amine and is protonated with an inorganic or organic acid and wherein the poly(dihydrobenzoxazine) is the reaction product of about 1 equivalent of a primary amine, about 1 equivalent of a phenol and about two equivalents of formaldehyde. The dispersions can be dried and cured to provide useful surface coatings and primers. The curing step occurs without evolution of volatile matter.

26 Claims, No Drawings

AQUEOUS DISPERSIONS OF POLYAMINES AND POLY(DIHYDROBENZOXAZINES)

This invention relates to aqueous resin dispersions and their use as coating compositions. In particular, this invention relates to aqueous dispersions comprising poly(dihydrobenzoxazines) and salts of polyamines, and to their application as primers and surface coatings.

Aqueous coating systems have been prepared in the past from polyamine salts of inorganic and organic acids. The polyamines generally contain hydroxy groups and are crosslinked by blocked isocyanates. In addition to the high temperature required to unblock the isocyanate, another undesirable aspect of such systems lies in the generation of volatiles which may be toxic, may contribute to oven-fouling or may affect coating properties adversely. Acid catalyzed crosslinkers such as amine aldehyde resins are also used in such systems but do not provide adequate cure response.

W. J. Burke et al (J. Org. Chem 30, 3423 (1965) and J. L. Bishop (Thesis, Univ. of Utah 1962) describe the potential reactions of dihydro-1,3-benzoxazines with a number of different types of compounds (HY) characterized by the presence of a highly nucleophilic carbon or nitrogen atom.

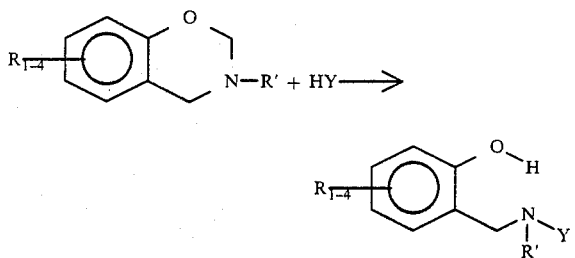

These ring opening aminoalkylation reactions as described by Burke and Bishop do not liberate volatiles. The reaction aptitude depends both on the structure of the 1,3-dihydrobenzoxazine and on the structure of the nucleophile containing molecule. Burke and Bishop do not include primary amines among the HY compounds, or secondary amines except for the heterocyclic secondary amines, indole aund carbazole which are incapable of providing polymerization systems. No polymerization reactions of dihydrobenzoxazines are described.

Rigterink describes the formation of poly(dihydrobenzoxazines) from various combinations of polymethylene diamines and phenols (U.S. Pat. No. 2,826,575) and from amines with bis-phenols (U.S. Pat. No. 2,825,728). These materials were used as parasiticides.

Burke et al [J. Am. Chem. Soc., 72, 4691 (1950) and J. Org. Chem., 26, 4403 (1961)] and Kuehne et al [J. Med. Pharm. Chem., 5, 257 (1962)] describe the formation of polybenzoxazines of polyhydric phenols and amines. The polymerization of these polybenzoxazines or their reaction with amines is not discussed or implied.

H. Schreiber (British Pat. No. 1,437,814) describes the preparation and use of dihydrobenzoxazine polymers and prepolymers. These materials are relatively slow curing by themselves and in the presence of resins and polymerizable compounds. Specifically, the heating of these materials both alone and with epoxy resins typically provides gel times of several hours at temperatures $>100°$ C.

The present invention provides a composition comprising an aqueous dispersion of a protonated reactive polyamine in the form of a salt of an organic or inorganic acid and a poly(3,4-dihydro-3-substituted-1,3-benzoxazine). The reactive polyamine contains primary and/or secondary amine groups. The dispersion is applied to substrates, and when it is heated the amine groups react with the dihydrobenzoxazine groups of the poly(dihydrobenzoxazine) to provide a cured composition.

The poly(dihydrobenzoxazines) are oligomeric mixtures wherein the majority of individual molecules contain at least two 3,4-dihydro-3-substituted-1,3-benzoxazine moieties and are capable of reacting with primary or secondary amines in the temperature range of about 25° to about 200° C., advantageously in times less than 30 minutes. The reaction between a dihydrobenzoxazine and an amine generates very little volatile matter since it involves a ring opening aminoalkylation reaction.

Aqueous dispersions which have long pot lives are obtained with blends of polydihydrobenzoxazines and cationic polyamine resins containing primary and secondary amine groups, which have been sufficiently neutralized with an acid. When the dispersions are dried and heated, and acid is volatilized, freeing the amine groups to react with the dihydrobenzoxazine groups. Another aspect of the invention is directed to the coating process and to substrates coated with the dispersions.

Although the dihydrobenzoxazines are formed from the condensation of phenol with amines and formaldehyde, they can be made essentially formaldehyde free and free from the potential of formaldehyde being liberated as a cure volatile. This is in contrast to existing commercial amino-formaldehyde and phenol formaldehyde crosslinking agents which do contain residual formaldehyde and/or liberate formaldehyde as a cure volatile. Furthermore, polydihydrobenzoxazines) in combination with polyamines will cure over a broad pH range. This includes the ability to cure in a highly basic pH environment. Conventional amino crosslinking agents are typically cured in the acid pH range and are very sluggish or slow curing at the high pH values associated with the presence of basic amine groups.

By selection of the polyamine and poly(dihydrobenzoxazine), cured coatings can be obtained which provide a wide range of coating properties, including chemical resistance, corrosion resistance, toughness, flexibility and hardness. By proper selection of the polyamine and the poly(dihydrobenzoxazine) a particular property or properties of the coating can be maximized to suit the end use of the cured film.

The ring opening aminoalkylation reaction of 3,4-dihydro-1,3 benzoxazine with an amine group produces a methylene diamine linkage.

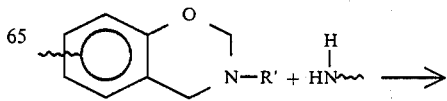

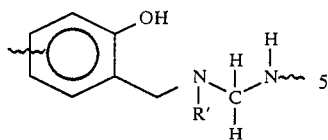

This methylene diamine bridge consisting of a single carbon joining two amine groups forms the major polymerization linkage when poly(dihydrobenzoxazines) are reacted with polyamines. Amine compounds where two amine nitrogen atoms are joined to a single carbon atom are generally regarded to be unstable and can usually be isolated only as their acid salts or in complex cyclic ring structures such as hexamethylene tetramine. In contrast, the cured compositions of the present invention comprising such diamine bridges possess surprising toughness, durability and excellent chemical resistance to solvents and corrosive environments. Thermal resistance of the cured systems is more than adequate for conventional protective coating applications.

The dihydrobenzoxazines are prepared by the condensation of a phenol, a primary amine and formaldehyde, the condensation product being substantially formaldehyde free and incapable of generating formaldehyde at the curing step. The base strength $pK_b$ of the primary amines may be in the range of 3 to 13. The poly(dihydrobenzoxazines) prepared from aromatic amines with $pK_b > 7$, generally yield mixtures, dispersions and solutions with polyamines which are more stable at room temperature yet cure more completely at lower temperatures than compositions of polyamines and poly(dihydrobenzoxazines) derived from more basic amines with $pK_b < 7$. This result runs contrary to the well known generalization that the aminoalkylation aptitude of a dihydrobenzoxazine increases with basicity of the amine from which the oxazine is derived.

A further surprising result is that if the dihydrobenzoxazine is derived from a weakly basic aromatic amine it can be combined with a polyamine, containing pendant primary and/or secondary amine groups, which has been protonated with sufficient acid to yield a stable aqueous dispersion. This stable dispersion can be coated on a substrate and cured at relative low temperatures to give solvent and corrosion resistant coatings. The dihydrobenzoxazines derived from the weak base aromtic amines show surprisingly good resistance to hydrolysis over extended time periods. Dihydrobenzoxazines prepared from the stronger base amines ($pK_b < 7$) also provide aqueous dispersions when combined with cationic aminofunctional resins but the dispersions are somewhat less stable since such dihydrobenzoxazines have a greater tendancy to hydrolyze or react with amine groups when they are maintained in aqueous media for long periods of time.

Poly(dihydrobenzoxazine) compounds suitable for admixture with polyamine compounds to provide the dispersions used in the present invention are advantageously of number average molecular weight in the range of about 250 to about 2000 and can be prepared by a variety of techniques from many types of coreactants. Many of the preferred dihydrobenzoxazines are oligomeric mixtures wherein the majority of individual molecules contain at least two 3,4-dihydro-3-substituted-1,3-benzoxazine groups. The dihydrobenzoxazines can be made by reacting about one equivalent of an amine containing at least two primary groups with about two equivalents of formaldehyde and about one equivalent of a monophenol containing at least one unsubstituted ortho position. Suitable di-primary amines include hydrazine, and $C_2$ to $C_{40}$ unsubstituted and substituted di-primary amines such as bis(aminophenyl)alkanes, diaminobenzenes, diaminoalkanes, diaminocycloalkanes and various polyoxyalkylene diamines. Suitable polyamines include poly(aminophenyl)alkanes, alkane polyamines and polyoxyalkylene polyamines. Diaminobenzenes and bis(aminophenyl)alkanes and higher oligomers are preferred amino reactants. The optional substituents of these di- and polyamines include alkyl, alkoxy, aryl and halo substituents. Examples of suitable phenols include $C_6$ to $C_{30}$ phenols such as phenol, alkyl phenols, alkoxy phenols, aryl phenols, halophenols, napthols and other aromatic hydroxy materials which have at least one unsubstituted position ortho to each hydroxy group and which may contain substituents such as alkyl, alkoxy, aryl or halo substituents which do not substantially deactivate these unsubstituted ortho positions and do not react with primary amine groups.

A second method for making poly(dihydrobenzoxazines) is by the reaction of an unsubstituted or substituted primary amine, and formaldehyde with a $C_6$ to $C_{70}$ polyphenol containing at least two hydroxysubstituted aromatic rings each with at least one unsubstituted position ortho to each hydroxy group optionally containing substituents such as alkyl, alkoxy, aryl or halo substituents which do not substantially deactivate the unsubstituted ortho positions and do not react with primary amines. The reaction ratio is typically about one equivalent of such polyphenol to one equivalent of primary amine, and two equivalents of formaldehyde. The equivalent of the polyphenol is based on the number of hydroxysubstituted aromatic rings containing at least one unsubstituted position ortho to the hydroxy groups. The primary amines may contain alkyl, alkoxy, aryl or halo substituents. Suitable primary amines contain from one to forty carbon atoms and include aminoalkanes, aminocycloalkanes, aminoalkenes, amino glycols, and arylamines such as aniline and naphthylamine. Aniline and substituted anilines are preferred amine reactants. Suitable polyphenols include hydroquinone, resorcinol and catechol, biphenols, naphthalenediols, phloroglucinol, bisphenols, novolac resins prepared from phenol and substituted phenols, and the alkyl, alkoxy, aryl and halo substituted derivatives of these polyphenols. Preferred polyphenols include hydroquinone, bisphenol A, bis(4-hydroxyphenyl)methane, 4-hydroxyphenyl ether, 4-hydroxyphenyl sulfone, and 4,4'-bisphenol and novolac oligomeric mixtures derived from the acid condensation of phenol with formaldehyde, of number average molecular weight less than about 1000.

A third method for preparing poly(dihydrobenzoxazines) is provided by the reaction of a mixture of any of the above listed monophenols and/or polyphenols with a mixture of any of the above listed monoamines and/or polyamines and formaldehyde to form oligomers of average molecular weight in the range of about 250 to about 2000, containing an average of at least about two dihydro-1,3-benzoxazine moieties per molecule. Many reaction combinations are possible but to maximize dihydrobenzoxazine formation, 1 phenol group and 2 molecules of formaldehyde should be present for each primary amine group in the reaction mixture.

The poly(dihydrobenzoxazine) portion of the composition of the present invention can consist of one type of dihydrobenzoxazine or a mixture of dihydrobenzoxazines derived from different phenols and/or different amines. These mixtures can be obtained either by blending already formed dihydrobenzoxazines or by forming mixed dihyrobenzoxazine products by using a blend of reactants as set forth hereinabove.

Generally in the preparation of dihydrobenzoxazine prepolymers 100% conversion of the amine reactant to dihydrobenzoxazine does not occur because of side reactions. The products of the side reactions are for the most part characterized by the formation of dibenzyl amine linkages between the ortho and para positions of adjacent phenol rings. Once these dibenzyl amine linkages form it becomes impossible for the bridged amine group to participate in heterocyclic dihydro-1,3-benzoxazine ring formation. For example, products typically formed from diamines with monophenol and formaldehyde or from diphenols with monoamines and formaldehyde, will contain the expected bis(dihydrobenzoxazines), but will also contain lesser amounts of higher molecular weight oligomers typically having at least two terminal dihydrobenzoxazine groups but also having one or more internal dibenzylamine linkage. Typical products made by the disclosed method will have 50 to 95% of the amine groups in the 3-position of the dihydrobenzoxazine ring. The remaining 5 to 50% of the amine groups will be principally in the form of dibenzylamine bridging. Another side reaction which can occur during and after dihydrobenzoxazine formation is the condensation of a formed dihydrobenzoxazine ring with a non-heterocyclized phenol ring containing an unreacted ortho or para ring position via an aminoalkylation reaction. This ring opening addition reaction results in dibenzylamine formation. These side reactions increase the molecular weight and may decrease the dihydrobenzoxazine functionality causing undesirable effects in the two component compositions of the present invention. These undesirable effects include reduced pot life and higher viscosity. Other side reactions are the conventional condensation of formaldehyde with phenols to form methylol groups and methylene bridges. These side reactions are controlled by the reaction method set forth herein.

Our preferred method for making dihydrobenzoxazines for use in this invention involves combining the phenol, amine and formaldehyde in the presence of a process solvent at temperatures which minimize the side reaction products. Aqueous formaldehyde can be added to a solution of amine and the phenol in the process solvent. In cases where the amine e.g. hexamethylene diamine reacts initially with formaldehyde to form crosslinked amine formaldehyde intermediates which are difficult to redissolve, it is preferable to make a dispersion of the phenol, process solvent and formaldehyde and add the amine or a solution of amine slowly to this dispersion. The process solvent is selected on the basis of its ability to dissolve the poly(dihydrobenzoxazine) reaction product and form immiscible phases with water and/or form azeotropic compositions with water. It is also desirable if possible for the process solvent to be a solvent for the two-component systems disclosed in this invention. Preferred solvents include methylene chloride, toluene, xylene and n-butanol or mixtures of these with themselves or other solvents. Many other solvent choices are possible. Other solvents can be added at the end of the process to make the poly(dihydrobenzoxazine) compatible with the polyamine component and to meet the requirements of the end use. Formaldehyde can be introduced in any of the forms which provide or generate formaldehyde such as aqueous formalin, formaldehyde in methanol, solid paraform or trioxane. Generally, concentrated aqueous formaldehyde solutions are preferred for economic reasons, but alcoholic formalin is often desirable when solubility problems are encountered during poly(dihydrobenzoxazine)formation. It is generally preferable to combine the reactants below 55° C. to minimize the undesirable side reaction of formaldehyde condensing with phenol to form methylol groups which can generate cure volatiles at the time of use. Such side reactions can also be minimized by reacting the primary amine with formaldehyde to form an amino formaldehyde intermediate which is then reacted with the phenol to form the dihydrobenzoxazine.

There is a distinct difference in the tendency of different dihydrobenzoxazine compositions to undergo reactions during processing. Dihydrobenzoxazines made from amines which are more basic ($pK_b < 7$) are more prone to side reactions during processing and consequently give lower dihydrobenzoxazine yields. Advantageously these dihydrobenzoxazines are processed in a temperature range of 20° to 70° C. Dihydrobenzoxazines based on amines with $pK_b > 7$ are less subject to side reactions and are advantageously processed in the 40° C. to 120° C. range. Advantageously after the addition of the reactants, which is done at the low end of the appropriate temperature range, the reaction is refluxed at an intermediate temperature in the appropriate range to maximize dihydrobenzoxazine formation. The reaction is then completed by removing water and unreacted monomers and possibly solvent at the middle to high temperature point of the appropriate reaction range. With a process solvent such as methylene chloride, the completed reaction mixture separates into two layers and the upper aqueous layer can be withdrawn. The methylene chloride and remaining water can then be removed by vacuum distillation. It is generally preferable to remove water by azeotropic distillation to increase the extent of reaction of the components forming the dihydrobenzoxazine and to minimize the loss of organic materials in the water layer. It is generally advantageous to use a stoichiometric excess of formaldehyde. This excess improves the conversion. An excess of 1 to 5% is preferable. The excess unreacted formaldehyde can be very efficiently removed with the water removed from the reaction mixture. Stripping of water and process solvent under reduced pressure also effectively removes unreacted formaldehyde. It is also sometimes desirable to use a slight excess in the range of about 1 to about 5 percent of the primary amine used to form the dihydrobenzoxazine above 1 equivalent for each phenolic hydroxyl. However, at least 2 equivalents of formaldehyde based on the total amine should be present to react with the amine.

The specific composition of the phenol and amine used to form the poly(dihydrobenzoxazine) can also significantly affect the yield and the potential for side reactions. For example, a para substituted phenol reactant reduces the level of ring opening amino alkylation side reactions.

The resulting poly(dihydrobenzoxazines) are also different in their property behavior depending on whether or not they are formed from a strongly basic or a weakly basic amine. There is probably not a sharp demarcation with increasing $pK_b$ but a gradual transition. In respect to these differences and the fact that the dihydrobenzoxazines derived from weakly basic amines show greater stability and are more resistant to side reactions and aging effects, it is an unexpected and a surprising result of this invention that these weakly basic amine products will react as fast or faster and often more completely than the strongly basic amine products with the polyamine components of the two component systems of the present invention.

Purified dihydrobenzoxazine oligomers can be used in the practice of this invention but they generally offer no significant advantages over the oligomers containing controlled levels of side reaction products. Also they are not as economical to make and consequently not as commercially viable.

The property differences obtained using dihydrobenzoxazines derived from weak base amines such as aniline can be accentuated and moderated even more by using substituted anilines. Substituent groups can increase or reduce the amine basicity within the $pK_b$ range of 7-13. Selected substitutents such as halo, alkyl, aryl etc. can be introduced for plasticization, melt viscosity control, flammability control, corrosion improvement etc. A general trend with benzoxazines derived from weak base aromatic amines such as anilines is that ring substituents which reduce the basicity of the amino nitrogen will reduce the cure rate of the benzoxazine but will increase the stability of the benzoxazine especially in an aqueous dispersion.

A large variety of polymers containing pendant primary or secondary amine groups can be employed as the coreactants for poly(dihydrobenzoxazines). Amine groups can be introduced into a variety of backbone polymer or oligomeric structures containing functional groups such as oxirane, isocyanate and carboxyl by reacting these materials under conditions well known to the art with low molecular weight polyamines or amine intermediates. For example polyamine compounds can be derived from diglycidyl ethers of bisphenol A polyethers, various aliphatic polyethylene or polypropylene glycol(diglycidyl ether) adducts, diglycidyl ether adducts of other polyols and glycidyl ethers of phenolic resins, such epoxy resins being commercially available. These polyamine polymers can also contain tertiary amine groups, which are not reactive with the dihydrobenzoxazine ring but which can contribute to the cationic performance of the resin system. The polyamine compounds will typically have number average molecular weights of 500 to 15,000 and preferably in the range of 800 to 5000 and become water dilutable after protonation with acids.

Amine groups can be attached to compounds having pendant carboxyl groups such as polyester, acrylic, and urethane by reacting with difunctional amines. Also free carboxyl groups can be reacted with alkyleneimine or substituted alkylene imine, as proposed in U.S. Pat. No. 3,679,564.

Blocked amines can be attached to backbone polymers and oligomers and subsequently transformed into primary amine groups. Such blocked amine groups can be attached to epoxy resins or acrylic resins having pendant oxirane groups by reacting a ketimine derived from reacting an excess of ketone with a polyamine containing at least one primary amine group and one secondary amine group. Blocked amines reacted with epoxy resins are described in U.S. Pat. No. 4,379,911. Blocked amines can also be reacted with carboxyl containing compounds such as dimerized fatty acids as described in U.S. Pat. No. 3,523,925.

Representative polyamine polymers containing pendant amine groups can be derived from epoxy and epoxy-modified diglycidyl ethers of bisphenol A structures, various aliphatic polyethylene or polypropylene glycol(diglycidyl ether) adducts, and glycidyl ethers of phenolic resins, such epoxy resins being commercially available. The preparation of adducts of polyepoxide resins and polyamines is described in detail in U.S. Pat. Nos. 4,093,594 and 4,116,900. Polyadducts of ammonia and epoxide compounds are described in U.S. Pat. No. 4,310,645.

Polyamine polymers containing pendant primary and secondary amine groups can be modified further by reacting them partially with monepoxides, diepoxides and other amine reactive reagents. These reactions can be used to alter the reactivity of the polyamine component with benzoxazines. Also, such reactions can be used to plasticize, flexibilize and otherwise modify the properties of the cured compositions.

Other useful polymers containing pendant amine groups include polyamide resins, for example, condensation products of dimerized fatty acids coreacted with difunctional amine, such as ethylene diamine to provide polyamines of molecular weight in the range of about 500 to about 5000. Further useful polymers containing pendant amine groups include acrylic resins, polyester resins, polyurethane resins and vinyl resins having molecular weights of about 1,000 to about 5,000.

The preferred polyamines containing pendant amine groups should contain at least two primary and/or secondary amine groups per molecule. High molecular weight pendant amine containing compounds should advantageously have about one pendant primary or secondary amine group for each 1500 units of molecular weight and preferably one pendant primary or secondary amine group for each 500-1000 units of molecular weight. For maximum speed of reaction of the dihydrobenzoxazine compound with the polyamine compound, the majority of the pendant amine groups should be primary amines. Cure speed can be regulated by varying the ratio of primary to secondary amine groups present in the molecule.

Aqueous solutions or dispersions made from the two component compositions are highly useful as coating compositions, applied by conventional coating techniques. It is necessary to add a neutralizing agent to obtain a suitable cationic aqueous composition. Neutralization is accomplished by reacting all or part of the amine groups with a water soluble organic or inorganic acid, preferably an acid which is water soluble such as formic acid, acetic acid, propionic acid, lactic acid, phosphoric acid, sulfuric acid, hydrochloric acid and the like. Organic acids which are aliphatic monocarboxylic acids having up to 4 carbon atoms are preferred.

The extent of neutralization depends upon the particular polyamine resin used. Advantageously, the neutralization should be sufficient to make a stable water solution or dispersion of the blend of protonated polyamine compound and poly(dihydrobenzoxazine). For greater dispersion aging stability arising in part from preferential protonation, a polyamine component containing stronger base amine groups ($pK_b < 5$) is blended with a poly(dihydrobenzoxazine) derived from a weak base amine ($pK_b > 8$). The polyamine component can also contain different levels of tertiary amine groups and even quaternary ammonium hydroxide groups which are not reactive with a dihydrobenzoxazine. However, these tertiary and quaternary groups may also have to be protonated with an acid in order to provide effective protonation of the reactive primary and secondary amine sites and improve stability. Examples XVIII-XX illustrate the effect of the "concentration" of acid and the excellent pot life obtained under the right conditions. Pot life as used herein refers to resistance of the dispersed composition to marked change in reology with time.

The term "dispersion" as used herein denotes a transparent, translucent or opaque disperion of polyamine and poly(dihydrobenzoxazine) in a continuous aqueous phase. The number average particle diameter of the resin phase is generally less than 10 and preferably less than 5 microns. A stable dispersion is one which does not settle or if some sedimentation occurs is easily redispersible and free of coagulum.

Prior to being formed into a dispersion, the two resin components are most conveniently handled as solutions in organic solvents. The poly(dihydrobenzoxazines) are generally soluble in the chlorinated hydrocarbons, aromatic hydrocarbons, cyclic ethers and the propyl and glycol ether solvents. Ketones such as methyl ethyl ketone and methyl isobutyl ketone can also be used as solvents. Mixed solvents can be used with the poly(dihydrobenzoxazines) and are often an advantage to give compatibility with various polyamine coreactants. Preferred solvents include the propyl and glycol ether solvents and mixtures of these with xylene, toluene and methyl isobutyl ketone. The polyamine components are generally soluble in the same solvents as the poly(dihydrobenzoxazine). The solvents are preferably selected so that they can function as coupling and coalescing solvents in the aqueous dispersions subsequently formed or so that they can be readily removed by azeotropic distillation techniques after the dispersions have been formed.

The poly(dihydrobenzoxazine) and polyamine solutions can be mixed and stored as a one package system or mixed just prior to forming an aqueous dispersion depending upon stability of their mixture. As disclosed herein, dihydrobenzoxazines derived from weakly basic amines generally form more stable solutions with polyamines than do dihydrobenzoxazines derived from strongly basic amines. Improved storage stability with certain poly(dihydrobenzoxazine) polyamine mixtures is achieved by blocking reactive primary amine groups of the polyamine by ketimine formation. When the mixture of poly(dihydrobenzoxazine) and ketimine blocked polyamine is dispersed in water containing the protonating acid, the ketimine unblocks and a stable dispersion forms. The salt forming or protonating acid can also be added to an organic solution of the polyamine followed by addition of the poly(dihydrobenzoxazine) and the blend of polyamine salt and poly(dihydrobenzoxazine) in organic solvent can then be dispersed in water to form a stable dispersion. Compositions of this invention can also be dispersed in the presence of or with the aid of, cationic or nonionic dispersing agents. Many varieties of these agents are commercially available and well known to those skilled in the art.

The aqueous dispersion of polyamine with poly(dihydrobenzoxazine) may contain up to about 30% by weight of organic solvents in order to reduce the viscosity, and to improve the flow and coalescing characteristics. Useful solvents include hydrocarbons, alcohols, esters, ethers and ketones. Solvents can be water soluble, partially water soluble or water insoluble organic solvents and mixtures of these. Examples of such solvents are 2-propanol, butanol, 2-ethyl hexanol, isophorone, 4-methoxy-2-pentanone, methyl-isobutyl ketone, toluene, xylene and the monoethyl, monobutyl and monohexyl ethers of ethylene glycol. It is generally desirable to maintain the organic solvent content as low as possible. Interfering or excess solvents present from the preparation of either the poly(dihydrobenzoxazine) or polyamine can be distilled off in vacuo prior to forming the aqueous dispersion or, in some cases after the dispersion is formed, by azeotropic distillation with water under vacuo with controlled heating.

It may sometimes be advantageous, in order to accelerate rapid and complete curing of the compositions of this invention, to include a catalyst in the coating mixture. Catalysts which catalyze urethane formation will catalyze the reaction of poly(dihydrobenzoxazine) and polyamine. Tin compounds such as dibutyltin dilaurate, dibutyltin diacetate and tin dioctoate are preferred, but other urethane catalysts may be employed. Metal salts and metal ion complexes may be used as catalysts if they are compatible with the cationic aqueous dispersions of this invention. The amount of catalyst employed is the amount which effectively promotes crosslinking of the deposited film, for example, amounts varying from about 0.1 percent to about 10 percent by weight of the composition may be employed. Typically about 2 percent by weight of the poly(dihydrobenzoxazine)-polyamine mixture is employed.

The aqueous dispersions of this invention can be used as coating compositions applied by conventional technique (e.g., dipping, spraying, brushing, roll coating, etc.) or advantageously by cathodic electrodeposition. Solids contents of about 30 to 60% by weight are useful for conventional methods of application. For cathodic deposition from a paint bath on to electrically conducting surfaces the solids content of the dispersion is usefully from about 5 to about 30% by weight, and preferably from about 10 to about 20% by weight, after dilution with water. Advantageously the pH-value of the aqueous dispersion lies in the range of about 3.0 to 9.0, preferably between 5.5 to 7.5. The amount of acid will vary but the concentration of acid for maximum stability will be at least about one equivalent of acid for each equivalent of reactive primary and secondary amine.

When the aqueous dispersion described herein is employed for use in electrodeposition, the aqueous dispersion is placed in contact with an electrically conductive anode and the electrically conductive cathode surface which is to be coated. A direct electric current is applied at an effective voltage, advantageously in the range of 25 to 500 volts for a time sufficient to subject the dispersion to electrophoresis to deposit a coating of the desired thickness generally in the range of about 12 to about 25 microns in thickness. The time required to build coatings in this thickness range is generally about 1 to 5 minutes. The temperature of the bath is generally maintained in the 20° to 30° C. range. The coated object is then removed from the bath, rinsed and baked at a suitable temperature generally selected in the range of 100° to 200° C. for 10 to 30 minutes to obtain a cured coating.

For electrodeposition and the other conventional coating applications the coating can be applied to a variety of electroconductive substrates especially metal such as steel, aluminum, copper, magnesium and the like, and metallized plastic, metal filled plastic and conductive carbon coated materials. For the other conventional coating applications, the compositions can also be applied to non-metallic substrates such as glass, wood and plastic.

The aqueous dispersions of the invention can be formulated with conventional additives if desired. For example antifoam agents, pigments, flow control agents, coupling solvents, coalescing solvents, plasticizers and antioxidants, surface active agents, etc., can be included so long as such materials are inert to the polydihydrobenzoxazinepolyamine compositions and do not enter into any undesirable reactions with water at an acidic to neutral pH-value or precipitate during aging in a form that cannot be redispersed or dissolved by stirring.

The pigment composition may comprise any of the conventional types, such as one or more pigments selected from the group consisting of iron oxides, lead oxides, strontium chromate, carbon black, titanium dioxide, kaolin, talc, barium sulfate, barium yellow, cadmium red, chromic green, lead silicate and the like. In the practice of this invention, the pigment to resin weight ratio is usually within the range of 0.02 to 1:1.

Many of the polyamine components of this invention when protonated with an acid can be used as effective dispersants for pigments. Typically 5 to 25 parts of cationic polyamine resin is used per 100 parts of pigment solids.

The relative proportions of poly(dihyrobenzoxazine) and polyamine components may fall within a wide range depending upon the particular composition of each of the components. For maximum cure response at least one dihydrobenzoxazine group is present to react with each pendant primary amine present in the polyamine. However, additional dihydrobenzoxazine groups may be present to react with the pendant secondary amines or with the secondary amine group which forms when a dihydrobenzoxazine reacts with a primary amine. In general, the amount of dihydrobenzoxazine functionality used is sufficient to react with enough of the primary and/or secondary amine groups present in the polyamine to result in crosslinking at elevated temperature cure to the extent desired or needed to obtain a suitable balance or combination of mechanical properties and solvent resistance. The amount of poly(dihydrobenzoxazine) may advantageously fall in the range of 02 to 2.0 equivalents of dihydrobenzoxazine group per equivalent of potential primary and/or secondary amine nitrogen in the polyamine. Typically on a weight basis the poly(dihydrobenzoxazine) will fall in a range of 5 to 50 parts of poly(dihydrobenzoxazine) per 100 parts of the combined weight of poly(dihydrobenzoxazine and polyamine.

The aqueous dispersions of this invention can also be used in combination with other crosslinking agents such as conventional aminoplast resins and blocked isocyanates. These crosslinking agents may in some cases be particularly advantageous in altering the cure behavior and crosslink density when used in combination with polyamines containing hydroxyl functionality as well as reactive amine functionality.

EXAMPLE I

PREPARATION OF DIHYDROBENZOXAZINE 1

To a suitably equipped glass resin reactor equipped with stirrer is charged 450 parts phenol, 450 parts methylene chloride and 144 parts of ethylene diamine. The temperature of the reaction mixture is adjusted to 25° C. and 595 parts of 50% formalin is added while maintaining the temperature below 30° C. The reaction mixture is stirred for 2 hours at 30° C. after formaldehyde addition is complete. It is then heated to atmospheric reflux, refluxed for 3 hours and allowed to cool and separate into two layers. The upper water layer is withdrawn and discarded. The lower organic layer is reheated to atmospheric reflux and distilled to remove solvent. Heating is continued with the gradual reduction of pressure until a temperature of 70° C. at about 5.0 kPa pressure is reached. Cellosolve (460 parts) is added to the resin slowly, keeping the temperature near 70° C. A uniform yellow solution forms which is cooled and filtered. The product has 66% closed dihydroxybenzoxazine ring and a calculated equivalent wt. of 224. The solution has a solids content of 60.2%.

EXAMPLES II-VIII

PREPARATION OF DIHYDROBENZOXAZINES 2-8

To a suitably equipped glass resin reactor equipped with stirrer are charged 100 parts of bisphenol A, 70 parts toluene and an aminobenzene compound in the amounts set forth for Examples II to VIII in Table I. The slurry is warmed and agitated to form a uniform solution. An inert nitrogen atmosphere is maintained over the reaction mixture. The temperature of the reaction mixture is adjusted to 50° C. and 108 parts of 50% formalin are added slowly, while the temperature is maintained at 50° to 55° C. After formalin addition is complete the reaction is refluxed at 65° C. for 2 hours under reduced pressure. The reaction is then heated to atmospheric reflux and the reflux condensate is permitted to separate into an aqueous phase and an organic phase in an oil/water separator. The organic phase of the condensate is returned to the reactor and the aqueous phase is removed. After about 83 parts of water are removed and the reaction temperature reaches 110° C., pressure is gradually reduced and toluene is removed from the reaction mixture. The temperature is allowed to rise to 116° C. at 7 kPa. The devolatilized resin is cooled and when the temperature reaches 100° C., an appropriate solvent or solvent mixture is charged. Typically solutions in the solids range of 65–85% are prepared. Properties of devolatilized resin obtained by this procedure are summarized in Table I.

TABLE I

EXAMPLES II-VIII

| Example | Benzoxazine | Amino benzene Reactant | Parts | % dihydro-[a] benzoxazine Ring | Calc.[b] Equiv. wt. | D.R. Cure @ 135° C. seconds |
|---------|-------------|------------------------|-------|--------------------------------|---------------------|-----------------------------|
| II | 2 | Aniline | 81.5 | 83% | 278 | 80 |
| III | 3 | Toluidine | 94.0 | 85% | 305 | 29 |
| IV | 4 | 2-chloroaniline | 112.0 | 83% | 320 | 371 |
| V | 5 | 4-n-butylaniline | 131.0 | 95% | 303 | 75 |
| VI | 6 | 3-aminobenzotrifluoride | 137.0 | 85% | 353 | >600 |

TABLE I-continued

EXAMPLES II-VIII

| Example | Benzoxazine | Amino benzene Reactant | Parts | % dihydro-[a] benzoxazine Ring | Calc.[b] Equiv. wt. | D.R. Cure @ 135° C. seconds |
|---|---|---|---|---|---|---|
| VII | 7 | 4-chloroaniline | 112.0 | 91% | 292 | — |
| VIII | 8 | 3,4-dichloroaniline | 142.0 | 81% | 370 | >600 |

[a]% Dihydrobenzoxazine ring and equivalent weight calculated from quantitative $^{13}$C Nuclear Magnetic Resonance data as described herein.

[b]D.R. cures are measured by blending 1.5 equivalents of benzoxazine with 1.0 equivalent of polyamine C, Example XVI in a 50% solids solution.

EXAMPLE IX

ALTERNATE METHOD FOR DIHYDROBENZOXAZINE 2

To a reactor are charged 66 parts of paraformaldehyde, 66 parts of methanol and 1 part of potassium hydroxide. The mixture is warmed and stirred until the paraform dissolves. While the temperature is maintained in the 25°-35° C. range, 93 parts of aniline are added to the paraform solution. Upon completion of the aniline addition the reaction is stirred for 15 minutes and then 114 parts of bisphenol A are added. The reaction is heated to atmospheric reflux and refluxed for 1 hour. After 1 hour, toluene (100 parts) is added to the reaction mixture while it is being cooled. A water layer forms which is removed. The toluene is removed by heating and applying reduced pressure until a temperature of 90° C. at 7 kPa pressure is reached. The appropriate solvent is added at this point. The devolitilized resin has a % closed dihydrobenzoxazine ring of 87%, and a calculated equivalent weight of 262.

EXAMPLE X

PREPARATION OF DIHYDROBENZOXAZINE 9

To a reactor are charged 100 parts of methylene dianiline, 200 parts of toluene and 208 parts of p-octyl phenol. The slurry is warmed and agitated to form a uniform solution. An inert nitrogen atmosphere is maintained over the reaction mixture. The temperature of the reaction mixture is adjusted to 60° C. and 131 parts of 50% formalin are added slowly, while the temperature is maintained at 60° to 65° C. After formalin addition is complete the batch is refluxed at 65° C. for 2 hours under reduced pressure. The batch is then heated to atmospheric reflux and the reflux condensate is permitted to separate into an aqueous phase and organic phase in an oil/water separator. The organic phase of the condensate is returned to the reactor and the aqueous phase is removed. When reaction temperature reaches 110° C., the pressure is gradually reduced and toluene is removed from the reaction mixture. The temperature is allowed to rise to 116° C. at 7 kPa pressure. The product can be removed as a tacky semisolid or dissolved in an appropriate solvent. The devolitilized product has a % closed dihydrobenzoxazine ring of 88%, and a calculated equivalent wt. of 374.

EXAMPLE XI

PREPARATION OF DIHYDROBENZOXAZINE 10

The reaction of Example IX is repeated except that 100 parts of p-phenylene diamine is substituted for the methylene dianiline and 174 parts of phenol for the octyl phenol. Two hundred and thirty seven parts of 50% formalin are used. The devolatilized product has a % closed dihydrobenzoxazine ring of 79% and a calculated equivalent wt. of 218.

EXAMPLE XII

PREPARATION OF DIHYDROXYBENZOXAZINE II

To a reactor are charged 110 parts of 2,4-bis(p-aminobenzyl)aniline (a technical grade by-product sold by E. I. duPont de Nemours & Co.), 94 parts of phenol, 160 parts of toluene and 40 parts of n-butanol. The reactor is inerted with nitrogen and heated to 60° C. with stirring to form a uniform solution. At 60° C. 128 parts of 50% formalin are added rapidly allowing the temperature to rise to atmospheric reflux (reflux temperature ~91° C.). The batch is refluxed for 3 hours during which time the reflux condensate is returned to the reactor. After 3 hours the reflux condensate is separated into an aqueous phase and organic phase in an oil water separator. The organic phase of the condensate is returned to the reactor and the aqueous phase is removed from the reaction mixture. The reaction temperature is allowed to go to 110° C. at atmospheric pressure. The solution of product is cooled and filtered. The product has a % closed dihydrobenzoxazine ring of 87% and a calculated equivalent weight of 263. The reddish product solution has a solids content of 59%.

EXAMPLE XIII

PREPARATION OF DIHYDROBENZOXAZINE 12

A phenolic novolac resin which has a number average molecular weight of 309, an average of 1.19 unsubstituted ortho positions per ring (measured by $^{13}$C NMR) and 4.56% phenol monomer content, is used to form a dihydrobenzoxazine. To a reactor are charged 102 parts of the novolac, 93 parts of aniline, 120 parts of toluene. The reactor is inerted with nitrogen and heated to form a uniform solution. The temperature is adjusted to 50° C. and 128 parts of 50% formalin are added slowly, while the temperature is maintained at 50° to 55° C. After formalin addition is complete the batch is refluxed at 65° C. for 2 hours under reduced pressure. The batch is then heated to atmospheric reflux and the water is removed azeotropically until the reaction temperature reaches 116° C. The solution is cooled. The product has a % closed dihydrobenzoxazine ring of 76% and a calculated equivalent weight of 289. The orange solution of product has a solids content of 72% and an unreacted phenol monomer content of 0.13%.

EXAMPLE XIV

PREPARATION OF POLYAMINE A

Four hundred and ninety seven parts of polyglycidyl ether of Bisphenol A (sold by Shell Chemical Co. under the tradename Epon 1001) possessing an epoxy equivalent weight of 497 is added to 300 parts of cellosolve in a reactor blanketed with a nitrogen atmosphere. One hundred parts of cyclohexane is added and the reaction mixture is refluxed at 60° C. under reduced pressure. The reaction mixture is dried by removing water as a cyclohexane azeotrope by use of a decanting trap in the distillate return line. When water evolution ceases, the cyclohexane is removed by reducing the pressure to 7 kPa while keeping the temprature near 60° C. When the cyclohexane removal is complete, 267 parts of the diketimine derived from 1 mole of diethylene triamine and 2 moles of methyl isobutyl ketone (as described in U.S. Pat. No. 3,523,925) are added. The reaction mixture is held at 60° C. for one hour and then heated to 120° C. and held for one hour. The batch is cooled to 80° C. and 36 parts of water are added to hydrolyze the ketimine. The pale yellow polyamine solution is cooled and filtered. The product has a calculated number average m.w. of 1200 and an equivalent weight based on primary amine of 300. The solids content of the product solution is 56%.

EXAMPLE XV

PREPARATION OF POLYAMINE B

The procedure of Example XIV is repeated except that at 60° C. under a dry nitrogen blanket, 186.3 parts of a monoketimine derived from 1 mole of 2-(2-aminoethylamino)-ethanol are added in place of the diketimine and the batch is heated to 120° C. where it is held for 2 hours. The batch is cooled and filtered. The product has a calculated molecular weight of 1202 and an equivalent weight based on primary amine of 601. The solids content of the product solution is 61%.

EXAMPLE XVI

PREPARATION OF POLYAMINE C

Eight hundred and sixty two parts of polyglycidyl ether of Bisphenol A (sold by Shell Chemical Co. under the tradename Epon 1004 F) possessing an epoxy equivalent weight of 862 is added to 400 parts of methyl isobutyl ketone and the mixture is stirred and heated to 60° C. to dissolve the epoxy resin while any water present is removed by azeotropic distillation under the reduced pressure. At 60° C. under a dry nitrogen blanket, methyl isobutyl ketone solution containing 267.4 parts of diketimine derived from one mole of diethylene triamine and two moles of methyl isobutyl ketone are added and the batch is heated to 120° C. where it is held for 2 hours. The batch is cooled to 80° C. and 36 parts of water are added and mixed in to hydrolyze the ketimine. At 60° C., 229 parts of an aliphatic mono glycidyl ether (sold by Ciba Geigy under the tradename Araldite DY027) possessing an epoxy equivalent weight of 229 is added. The reaction mixture is held at 60° C. for 1 hour and then cooled and filtered. The product has a calculated number average molecular weight of 2388 and an equivalent weight based on primary amine of 1194. The pale yellow solution has a solids of 63.8%.

EXAMPLE XVII

PREPARATION OF POLYAMINE D

The procedure of Example XVI is repeated except in place of the Araldite DY027, 280 parts of a butyl glycidyl ether (sold by Ciba Geigy under the tradename Araldite RD-1) possessing an epoxy equivalent weight of 140 are added. After adding the monoepoxide at 60° C. and holding for two hours, the reaction mixture is cooled and filtered. The product has a calculated number average molecular weight of 2490 and is high in secondary amine content. The pale yellow solution has a solids of 67.6%.

EXAMPLE XVIII

The influence of the degree of protonation of the aminofunctional polymer and the critical level of protonation required for optimum stability is demonstrated by combining polyamine A (Example XIV) with polybenzoxazine 2 (Example II). The equivalence ratio of the polyamine/benzoxazine is kept constant at 1.0/0.7. Polyamine A and benzoxazine 2 are mixed together in ethylene glycol monoethyl ether (cellosolve) solvent at a 60–80% solids level. This concentrate is added under high shear mixing to deionized water containing the equivalents of acid, set forth in Table II. The resulting dispersions are made at, or adjusted to, a final 15% solids. The dispersions are maintained at 25° C. and their dry rubber cure characteristics followed with time. The degree of decrease in the dry rubber cure time on aging is directly related to the amount of benzoxazine/polyamine interaction that has occurred in the dispersion on aging. The data in Table II show that maximum stability occurs when at least one equivalent of acid is added for each equivalent of primary amine in Polyamine A. (Example XVIIIA; Table II) The aging stability rapidly decreases if less than one equivalent of acid is added to polyamine A. (Examples XVIII B and C; Table II). When only 0.5 equivalent of acid is added for each equivalent of primary amine in Polyamine A, the dry rubber cure falls to 0 in only 7 days indicating extensive reaction between polyamine and benzoxazine (Example XVIIID; Table II).

Polyamine A also contains two non reactive tertiary amine sites per polyamine molecule. Only one hydrogen ion is required to deactivate two basic amine sites separated by two carbon atoms toward reaction with a benzoxazine. Consequently, the diethylene triamine end groups present in polyamines A, C or D require a maximum of only two hydrogen ions for each of the three basic sites in the diethylene triamine group to reach the critical level of protonation for benzoxazine dispersion aging stability. Polyamine B requires only one hydrogen ion for each two basic end groups sites.

TABLE II

EFFECT OF ACID LEVEL ON THE STABILITY OF POLYAMINE A/BENZOXAZINE 2 DISPERSIONS @ 25° C.[a]

| Example | Equivalents Ratio[b] Acid/primary Amine | pH | D.R. Cure @ 135° C., seconds[c] | | | | |
|---|---|---|---|---|---|---|---|
| | | | 0 Days | 5 Days | 10 Days | 20 Days | 30 Days |
| XVIII A | 1.0/1.0 | 5.0 | 138 (100) | 136 (99) | 134 (97) | 131 (95) | 128 (93) |
| XVIII B | 0.9/1.0 | 6.6 | 122 (100) | 107 (88) | 94 (77) | 76 (62) | 68 (56) |
| XVIII C | 0.75/1.0 | 7.1 | 98 (100) | 86 (88) | 74 (76) | 54 (55) | 42 (43) |
| XVIII D | 0.50/1.0 | 8.4 | 51 (100) | 5 (10) | 0 (0) | 0 (0) | 0 (0) |

[a] One equivalent of polyamine A based on primary amine content added to each 0.7 equivalent of active benzoxazine ring in Benzoxazine 2. (Weight Ratio 60/40 PA/B). Dispersions made up to 15% solids in water with appropriate level of acid.
[b] Equivalent of lactic acid added for each equivalent of primary amine in polyamine A. pH of 15% dispersion is set forth.
[c] D.R. cure measured after storing 15% dispersions for indicated time at 25° C. Value in parenthesis is % of original D.R. cure value.

EXAMPLE XIX

The effect of degree of protonation on polyamine/benzoxazine stability is demonstrated further by the data in Table III obtained by combining polyamine B Example XV with benzoxazine 2, Example II, at an equivalence ratio of polyamine to benzoxazine of 1.0/1.4. The compositions are made into dispersions at 15% solids by the method of Example XVIII. The critical level of protonation is obtained at 1.0 equivalent of added acid to each equivalent of primary amine. Adding 50 or 100% excess acid above a 1/1 equivalent ratio does not significantly change the aging characteristics of the dispersion. In principle this means that once the critical level of protonation is achieved additional acid will not significantly improve the aging stability further. (Table III; A, B and C)

TABLE III

EFFECT OF ACID LEVEL ON THE STABILITY OF POLYAMINE B/BENZOXAZINE 2 DISPERSIONS @ 25° C.[a]

| Example | Equivalents Ratio[b] Acid/Primary Amine | pH[b] | D.R. @ 135° C., seconds[c] | | | |
|---|---|---|---|---|---|---|
| | | | 0 days | 30 days | 60 days | 90 days |
| XIX A | 1.0/1.0 | 6.8 | 191 (100) | 183 (96) | 181 (95) | 180 (94) |
| XIX B | 1.5/1.0 | 5.0 | 202 (100) | 191 (95) | 186 (92) | 185 (92) |
| XIX C | 2.0/1.0 | 4.1 | 211 (100) | 197 (93) | 191 (91) | 188 (89) |

[a]One equivalent of polyamine A based on primary amine content added to each 1.4 equivalent of active benzoxazine ring in Benzoxazine 2. (Weight Ratio 60/40 PA/B). Dispersions made up to 15% solids in water with appropriate level of acid.
[b]Equivalent of lactic acid added for each equivalent of primary amine in polyamine B. pH of 15% dispersion as indicated.
[c]D.R. cure measured after storing 15% dispersions for indicated time at 25° C. Value in parenthesis is % of original D.R. cure value.

EXAMPLE XX

The effect of the degree of protonation on polyamine C, Example XVI, which contains both reactive primary and secondary amines, when dispersed with benzoxazine 2, Example II is shown in Table IV. In this case the critical level of acid corresponds to one acid equivalent for each combined equivalent of primary and secondary amine (Table IV, Example XX A). A tertiary amine is also present in the bound ethylene triamine end groups of polyamine C but additional acid is not required to protonate this amine for reasons mentioned in Example XVIII. Dispersion of the polyamine/benzoxazine concentrate is accomplished as described in Example XVIII. Polyamine C/Benzoxazine 2 dispersions containing only 0.5 equivalent per 1.0 equivalent of reactive amine are less stable (Table IV, Example XV B). However, polyamines with increasing secondary amine contents show increasing dispersion stability over polyamines with all primary amines and less than the critical level of protonation (XVIIID Table II).

The difference in dispersion stability when comparing Benzoxazine 1 derived from a strong base amine and Benzoxazine 2 derived from a weak base amine, each combined with polyamine C and protonated to the same extent with acid, is shown in Table IV. The strong base amine Benzoxazine 1 gives a dispersion which falls off in D.R. cure time very quickly (Table IV; Example XXC) compared with the weak base Benzoxazine 2 (Table V; Example XXB) which shows a slower fall off.

TABLE IV

EFFECT OF ACID LEVEL ON THE STABILITY OF POLYAMINE CVERSUS BENZOXAZINES 1 AND 2.[a]

| Example | Ben-zoxa-zine | Equivalents Ratio[b] Acid/Primary and Secondary Amine | D.R. @ 135° C., seconds[c] | | | | |
|---|---|---|---|---|---|---|---|
| | | | 0 days | 10 days | 30 days | 60 days | 90 days |
| XX A | 2 | 1.0/1.0 | 162 (100) | 156 (96) | 150 (93) | 144 (89) | 139 (86) |
| XX B | 2 | 0.5/1.0 | 114 (100) | 95 (83) | 60 (53) | 16 (14) | 0 0 |
| XX C | 1 | 0.5/1.0 | 225 (100) | 114 (51) | 49 (22) | 0 0 | 0 0 |

[a]One equivalent of polyamine C based on primary amine content added to each 1.5 equivalent of active benzoxazine ring in Benzoxazines 1 and 2.
[b]Equivalent of lactic acid added for each equivalent of primary amine in Polyamine A.
[c]D.R. cure measured after storing 15% dispersions for indicated time at 25° C. Value in parenthesis is % of origingal D.R. cure value.

EXAMPLE XXI

PIGMENT PASTE RESIN AND FORMULATION (This example illustrates the use of a polyamine resin as an effective pigment dispersant). Eight hundred and sixty two parts of polyglycidyl ether of Bisphenol A (sold by Shell Chemical Co. under the trade name Epon 1004 F) possessing an epoxy equivalent weight of 862 is dissolved in 489 parts of butyl Cellosolve dried with cyclohexane as described in Example XIV. This solution is then reacted with 360 parts of a ketimine derived from one equivalent of methyl isobutyl ketone and N-coco-1,3-diaminopropane prepared according to the procedure set forth in Example XIV. After hydrolysis of the ketimine reaction product, excess methyl isobutyl ketone is removed. The final product is diluted with butyl Cellosolve to 50% solids.

One hundred and seventy six parts of the above 50% polyamine solution is blended with 4.8 parts of a nonionic surfactant sold by Airco Chemicals and Plastics Co. under the tradename Surfynol TG and 8.6 parts of 85% lactic acid. The mixture is then diluted with 100.6 parts of water. A pigment paste is prepared using 290 parts of this polyamine dispersant, 308 parts by weight of talc, 88 parts of lead silicate and 44 parts of carbon black and a final dilution with an additional 248 parts of water. (All parts are on a weight basis). The pigment slurry is ground in a suitable mill to a Hegman No. 7 fineness.

EXAMPLE XXII

ELECTROCOATING CLEAR FILMS (a) 207 parts of polyamine D from Example XVII at 67.6% solids are mixed with 2.0 parts Surfynol 104A surfactant, 10 parts of hexyl Cellosolve and 74.8 parts of Benzoxazine 2 (Example II) at 80.2% solids in methyl isobutyl ketone. This mixture is added to 360 parts of deionized water containing 12.7 parts of deionized water containing 12.7 parts of 80% lactic acid, under high shear mixing. The dispersion at 30% lactic acid, under high shear mixing. The dispersion at 30% solids is vacuum azeotroped under mild heat to remove methyl isobutyl ketone. The dispersion is then diluted to 20% solids. The pH is 5.21, the conductivity is 1458 μmhos. Zinc phosphated steel panels are coated with the mixture at 350 volts and 26° C. for 2 minutes (Rupture voltage ~370 volts). After baking for 20 minutes at 163° C., clear, hard, solvent-resistant coatings about 14 micron thick are obtained.

(b) The procedure of part (a) is repeated using 79.6 parts of Benzoxazine 6 from Example VI at 73.4% solids in methyl isobutyl ketone. The pH of the 20% solids dispersion is 5.85, the conductivity is 1772 μmhos. Zinc phosphated steel panels are coated with the dispersion at 275 volts and 26° C. for 2 minutes. Clear, hard coatings about 12.5 micron thick are obtained with properties similar to (a).

EXAMPLE XXIII

ELECTROCOATING PIGMENTED FILMS

A paint dispersion preblend is prepared from 705.3 parts of polyamine C solution described in Example XVI at 63.8% solids, protonated with 66.7 parts of 80% lactic acid and blended with 6.0 parts of Surfynol 104A surfactant and 30.0 parts of hexyl Cellosolve and lastly 185.4 parts of an 80.9% solids methyl isobutyl ketone solution of Benzoxazine 2 from Example II. This blend is added to 950 parts of water under high shear mixing to form a homogeneous dispersion at 33.5% solids. The methyl isobutyl ketone is azeotropically removed from the dispersion under reduced pressure and mild heating to yield a 37.9% low solvent dispersion.

A cathodic electrodeposition composition is prepared by blending 1500 parts of low solvent dispersion with 273 parts of pigment grind from Example XXI and with 1750 parts of water to give a dispersion of 20% solids having approximately 16 weight percent pigment based on total solids. This material is electrocoated on zinc phosphated steel panels at 275 volts and 28° C. for 2 minutes. After baking for 20 minutes at 135° C., clear, hard, solvent-resistant coatings of about 15 micron are obtained. The coating survives more than 200 MEK double rubs and has less than 1.25 mm scribe creep in 500 hr. salt spray corrosion tests.

Dry Rubber Cure Test

The Dry Rubber Cure Test (D.R. Cure) is used as a basis of comparison of the relative time to gelation of various dihydrobenzoxazine/polyamine compositions. The test is also used to follow aging (advancement) of these compositions with time. The test involves placing 4 to 5 drops of the composition being tested on the center of a flat cure plate controlled at 135° C. A flat 12.2 mm stainless steel spatula is used to spread and butter the compositions over a 25.4 mm diameter area. The time in seconds is recorded from the initial placement on the hot plate until the composition ceases the flow (string) when buttered with the spatula and becomes a rubbery film no longer movable with the spatula.

Carbon-13 Nuclear Magnetic Resonance Spectrometry of Dihydrobenzoxazine Structure Carbon spectra are recorded with a JEOL FX90Q spectrometer at room temperature. Dihydrobenzoxazines are preferably dissolved in chloroform or carbon tetrachloride solvents. Typically solution concentrations in the 30–50% solids range are run. The JEOL FX90Q is equipped with an external Li lock. Quantiative NNE measurement conditions are as follows: Field=22.5 MH$_z$, sample tube Q=10 mm, sweep width=5000 H$_z$, pulse width=20 microseconds, accumulation=2K, acquisition time=0.819 sec., pulse delay=30 seconds.

Chemical shifts are related to TMS (0 ppm) and expressed in ppm. Assignments are based on known literature references and values measured on model compounds by methods well known to those skilled in the art. The dihydrobenzoxazine carbons are numbered conventionally.

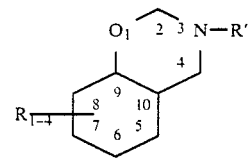

By comparing the carbon at ring position number 9, in a closed ring (~150–154 ppm) relative to the same carbon with the benzoxazine ring open and a —OH group attached (~154–157 ppm) a direct measure of % closed ring benzoxazine is obtained. Measurement of the carbon at ring position number 2, at 7.9 ppm when R′ is a benzenoid ring or at 8.2 ppm when R′ is a typical alkyl substituent also provides a direct measure of closed benzoxazine ring content. The quantitative relation of these carbons to the rest of the dihyrobenzoxazine carbons can be used to calculate both a % dihydrobenzoxazine content and an effective equivalent weight based on ring content. As those skilled in the art can readily appreciate, the nature of the substituents R and R′ and the nature of various side reaction products result in other chemical shifts in the NMR spectra. The assignment of these shifts depends on the structure of the particular benzoxazine and can be used to measure many other structural features of a particular dihydrobenzoxazine.

We claim:

1. An aqueous dispersion comprising a poly(3,4-dihydro-3-substituted-1,3-benzoxazine) and a protonated reactive polyamine, wherein the poly(dihydrobenzoxazine) is of number average molecular weight in the range of about 250 to about 2000, with the majority of the individual molecules containing at least two dihydrobenzoxazine groups, and is the reaction product of about 1 equivalent of a primary amine selected from the group consisting of mono- and poly-primary amines, about 1 equivalent of a phenol selected from the group consisting of mono- and poly-phenols having phenolic hydroxy groups with at least one unsubstituted position ortho to such hydroxy groups and about 2 equivalents of formaldehyde, wherein the protonated reactive polyamine is at least difunctional, the reactive groups being primary or secondary amine and wherein protonation is supplied by an inorganic or organic acid.

2. The dispersion of claim 1 wherein the poly(dihydrobenzoxazine) provides about 0.2 to 2.0 equivalents of dihydrobenzoxazine per equivalent of reactive polyamine.

3. The dispersion of claim 2 wherein the reactive polyamine is of number average molecular weight in the range of about 500 to about 15,000 and has a reactive amine equivalent weight in the range of about 250 to about 1500.

4. The dispersion of claim 1 wherein the primary amine reactant for the production of the poly(dihydrobenzoxazine) is an amine of pK$_b$ less than about 7.

5. The dispersion of claim 1 wherein the primary amine reactant for the production of the poly(dihydrobenzoxazine) is an amine of pK$_b$ at least about 7.

6. The dispersion of claim 5 wherein the primary amine reactant is a $C_6$ to $C_{40}$ unsubstituted or substituted aromatic amine.

7. The dispersion of claim 4 wherein the primary amine reactant is a $C_1$ to $C_{40}$ unsubstituted or substituted aliphatic amine.

8. The dispersion of claim 4 wherein the phenol reactant for the production of the poly(dihydrobenzoxazine) is a $C_6$ to $C_{30}$ phenol or a $C_6$ to $C_{30}$ phenol containing alkyl, alkoxy, aryl, or halo substituents, or a $C_6$ to $C_{70}$ polyphenol or a $C_6$ to $C_{70}$ polyphenol containing alkyl, alkoxy, aryl or halo substituents.

9. The dispersion of claim 5 wherein the phenol reactant for the production of the poly(dihydrobenzoxazine) is a $C_6$ to $C_{30}$ phenol or a $C_6$ to $C_{30}$ phenol containing alkyl, alkoxy, aryl, or halo substituents, or a $C_6$ to $C_{70}$ polyphenol or a $C_6$ to $C_{70}$ polyphenol containing alkyl, alkoxy, aryl or halo substituents.

10. The dispersion of claim 1 wherein there is present about one equivalent of protonating acid for each equivalent of reactive amine group in the reactive polyamine.

11. The dispersion of claim 1 wherein the protonating acid is a carboxy acid.

12. The dispersion of claim 1 wherein the protonating acid is a $C_1$ to $C_4$ carboxy acid.

13. An aqueous dispersion comprising a poly(1,3-dihydro-3-substituted-1,3-benzoxazine) and a protonated reactive polyamine wherein the poly(dihydrobenzoxazine) is the reaction product of about 1 equivalent of a weak base primary amine of $pK_b$ of about 7 or greater, about 1 equivalent of a $C_6$ to $C_{70}$ polyphenol selected from the group consisting of unsubstituted polyphenols and polyphenols substituted with alkyl, alkoxy, aryl or halo substituents and having at least two phenolic hydroxy groups with at least one unsubstituted position ortho to each such phenolic hydroxy groups and about 2 equivalents of formaldehyde, wherein the protonated reactive polyamine is at least difunctional, its reactive groups being primary or secondary amine of $pK_b$ less than about 5, and wherein protonation is supplied by an inorganic or organic acid.

14. The dispersion of claim 13 wherein the $C_6$ to $C_{30}$ polyphenol is selected from the group consisting of hydroquinone, bisphenol A, bis(4-hydroxyphenyl)methane, 4-hydroxyphenyl ether, 4-hydroxyphenyl sulfone, 4,4'-bisphenol and novolac resins.

15. The dispersion of claim 13 wherein there is present about one equivalent of protonating acid for each equivalent of reactive amine group in the reactive polyamine.

16. The dispersion of claim 13 wherein the protonating acid is a carboxy acid.

17. The dispersion of claim 13 wherein the protonating acid is a $C_1$ to $C_4$ carboxy acid.

18. A substrate coated with the dried and polymerized dispersion of claim 1.

19. A substrate coated with the dried and polymerized dispersion of claim 4.

20. A substrate coated with the dried and polymerized dispersion of claim 5.

21. A substrate coated with the dried and polymerized dispersion of claim 10.

22. A substrate coated with the dried and polymerized dispersion of claim 12.

23. A substrate coated with the dried and polymerized dispersion of claim 13.

24. A substrate coated with the dried and polymerized dispersion of claim 14.

25. A substrate coated with the dried and polymerized dispersion of claim 15.

26. A substrate coated with the dried and polymerized dispersion of claim 17.

* * * * *